United States Patent [19]

Takagawa et al.

[11] 4,311,867
[45] Jan. 19, 1982

[54] PROCESS FOR ISOMERIZING HYDROCARBONS

[75] Inventors: Makoto Takagawa; Tamotsu Ueno; Takehiko Takahashi, all of Niigata, Japan

[73] Assignee: Mitsubishi Gas Chemical Company, Inc., Tokyo, Japan

[21] Appl. No.: 142,062

[22] Filed: Apr. 21, 1980

[30] Foreign Application Priority Data

Apr. 20, 1979 [JP] Japan .................................. 54-48607

[51] Int. Cl.$^3$ ................................................ C07C 5/13
[52] U.S. Cl. ...................................... 585/736; 585/740
[58] Field of Search ................................. 585/736, 740

[56] References Cited

U.S. PATENT DOCUMENTS

| | | | |
|---|---|---|---|
| 2,461,541 | 2/1949 | Frey ....................................... | 585/371 |
| 2,461,545 | 2/1949 | Hepp ...................................... | 585/736 |
| 2,461,568 | 2/1949 | Richmond ............................. | 585/740 |
| 2,461,598 | 2/1949 | Gibson ................................... | 585/740 |
| 2,513,103 | 1/1950 | Passino .................................. | 585/740 |
| 2,583,740 | 1/1952 | Kemp .................................... | 585/736 |
| 3,786,108 | 1/1974 | Giannetti et al. .................... | 585/740 |

FOREIGN PATENT DOCUMENTS 604377 7/1948 United Kingdom .

OTHER PUBLICATIONS

McCaulry, JACS, vol. 81, pp. 6437–6443, Dec. 20, 1959.

Primary Examiner—Curtis R. Davis
Attorney, Agent, or Firm—Armstrong, Nikaido, Marmelstein & Kubovcik

[57] ABSTRACT

Unbranched or less branched paraffins having 6 carbon atoms as essential components are isomerized without side reaction in high yield in the presence of hydrogen fluoride and boron trifluoride as a catalyst while keeping percent isomerization of paraffins having 6 carbon atoms lower than the equilibrium percent isomerization of the paraffins having 6 carbon atoms at a given reaction temperature, or by conducting isomerization at a plurality of stages while keeping a reaction temperature at a given stage lower than that at the preceding stage and keeping percent isomerization of paraffins having 6 carbon atoms at a given stage lower than the equilibrium percent isomerization thereof at the reaction temperature at the stage.

15 Claims, No Drawings

PROCESS FOR ISOMERIZING HYDROCARBONS

This invention relates to a process for isomerizing hydrocarbons, and more particularly to a process for isomerizing paraffins, which comprises isomerizing unbranched paraffins or less branched paraffins as a raw material in the presence of a catalyst consisting of hydrogen fluoride and boron trifluoride (which will be hereinafter referred to as HF—BF$_3$) into more branched paraffins having a high octane number than the raw material paraffins.

Heretofore, metal compounds such as lead and manganese compounds have been used as an additive for increasing the octane number of gasoline, but the addition of such metal compounds is going to be abolished from the viewpoint of preventing the environmental pollution. As a substitute for these metal compounds, aromatic hydrocarbons such as benzene, toluene, xylene, etc. have been used. On the other hand, processes for isomerizing paraffins, thereby producing isoparaffins having a high octane number, and using the isoparaffins as a fundamental component for gasoline have been regarded as important. The present invention relates to a process for isomerizing the paraffins.

As the catalyst for isomerizing the paraffins, aluminum chloride, hydrogen chloride-aluminum chloride, HF—BF$_3$, hydrogen fluoride-antimony pentafluoride, etc. are well known. The present invention relates to a process for isomerizing paraffins containing paraffins having 6 carbon atoms as essential components in the presence of HF—BF$_3$ as a catalyst.

In the isomerization of paraffins containing paraffins of 5 to 6 carbon atoms as the main component in the presence of HF—BF$_3$ as the catalyst, decomposition and polymerization of raw material paraffins and the desired product isoparaffins take place with increasing conversion of the raw material paraffins and further decomposition and polymerization of the resulting decomposition and polymerization products take place as side reactions, and finally these side reactions become dominant and vigorous decomposition and polymerization take place. The by-products formed by such decomposition and polymerization include low boiling hydrocarbons having not more than 3 carbon atoms, which are hard to use as a gasoline fraction, high boiling hydrocarbons having a high degree of unsaturation, etc. Most of the high boiling hydrocarbons having a high degree of unsaturation dissolve into the catalyst layer, and considerably lower the isomerization activity of the catalyst. That is, in the isomerization of fresh paraffins containing paraffins having 5 and 6 carbon atoms as the main component in the presence of the catalyst layer that has experienced such vigorous decomposition and polymerization reactions, the decomposition and polymerization reactions are dominant, or the reaction itself is retarded. Ultimately, the desired isomerization reaction hardly proceeds in any case.

In the isomerization of paraffins in the presence of HF—BF$_3$ as a catalyst it is known that naphthenes, aromatic hydrocarbon and hydrogen each can suppress said various side reactions. However, they also have an action to suppress the isomerization reaction, and particularly aromatic hydrocarbons and hydrogen have the considerable action.

The present inventors have found that they have the action to suppress these side reactions only in a case of not relatively high conversion of raw material paraffins, but have not the action to supress the vigorous decomposition and polymerization reactions taking place in a case of high conversion. That is, for example, when one part by weight of n-hexane as raw material paraffin was isomerized in the presence of 1.5 parts by weight and 0.6 parts by weight of HF—BF$_3$ as the catalyst using 0.1 part by weight of cyclohexane as a side reaction-suppressing agent and 0.001 part by weight of 1-hexene as a reaction initiator or as a reaction promoter at a reaction temperature of 50° C., butanes and pentanes as decomposition products were hardly observed 100 minutes after the start of isomerization reaction, but when the isomerization reaction was further continued vigorous decomposition and polymerization reactions took place suddenly 120 minutes after the start of isomerization reaction, whereby more than 50% of the raw material n-hexane was converted to hydrocarbons having different numbers of carbon atoms such as propane, butane, high boiling hydrocarbons having 7 or more carbon atoms, and also the catalyst layer contained a large amount of high boiling hydrocarbons. Cyclohexane and its isomerization product, methylcyclopentane, were hardly observed in the reaction product solution.

An increase in the conversion of the raw material paraffin is necessary for obtaining a product with a high octane number, but, on the other hand, brings about the vigorous decomposition and polymerization reactions as mentioned above.

As a result of extensive studies of suppressing the vigorous decomposition and polymerization reactions and increasing the conversion of the raw material paraffin, the present inventors have accomplished the present invention. That is, the present inventors have studied conditions for causing the vigorous decomposition and polymerization in detail, and have found that, in the isomerization of paraffins containing paraffins having 5 and 6 carbon atoms as the main component it is the paraffins having 6 carbon atoms that mainly causes the vigorous decomposition and polymerization reactions, whereas the paraffins having 5 carbon atoms hardly cause the vigorous decomposition and polymerization reaction, though some of them undergo disproportionation to paraffins having 4 to 6 carbon atoms, and that the occurrence of the vigorous decomposition and polymerization reactions have nothing to do with the amount of HF—BF$_3$ as the catalyst, reaction temperature, the kind and amount of the so far well known reaction initiator or promoter such as olefins and paraffins having 8 or more carbon atoms, and the kind and amount of so far well known side reaction-suppressing agent, but such reactions are suddenly brought about only when the percent isomerization of the paraffins having 6 carbon atoms in the reaction solution reaches the equilibrium percent isomerization at a given reaction temperature, and very less side reaction occurs until the equilibrium has been reached, and that this phenomenon is peculiar to the paraffins having 6 carbon atoms, and, for example, even if the percent isomerization of the paraffins having 5 carbon atoms reaches the equilibrium percent isomerization at a given reaction temperature, any side reaction hardly takes place. The present invention is based on the foregoing finding.

An object of the present invention is to provide a process for isomerizing hydrocarbons, where unbranched, or relatively less branched paraffins having 6 carbon atoms as essential components are isomerized in the presence of HF—BF$_3$ as a catalyst, characterized by conducting the isomerization while keeping a percent isomerization of the paraffins having 6 carbon atoms lower than the equilibrium percent isomerization of the paraffins having 6 carbon atoms at a given reaction temperature.

Any paraffins can be used as raw material in the present invention, so long as they contains unbranched or relatively less branched paraffins having 6 carbon atoms as essential components, and, in addition to the paraffins having 6 carbon atoms, they can contain any of paraffins having 5 or less carbon atoms, aromatic hydrocarbons such as benzene, etc., paraffins having 7 or more carbon atoms, and naphthenes.

It is preferable that the raw material paraffins contain aromatic hydrocarbons and naphthenes, because they have an action to suppress the side reaction in a case of low conversion of the raw material paraffins. On the other hand, aromatic hydrocarbons and naphthenes each have also an action to suppress the isomerization of the raw material paraffins, and thus it is preferable that the raw material paraffins contain not more than 2% by weight of aromatic hydrocarbons and 1 to 40% by weight of naphthenes.

It is also preferable that the raw material paraffins contain paraffins having 7 or more carbon atoms, because they have an action as a reaction initiator or promoter in the present reaction system. However, a larger content of the paraffins having 7 or more carbon atoms in the raw material will promote side reactions such as decomposition and polymerization, and accordingly, it is preferable that the raw material paraffins contain 1 to 20% by weight of paraffins having 7 carbon atoms, 0.1 to 1% by weight of paraffins having 8 carbon atoms, and not more than 0.1% by weight of paraffins having 9 or more carbon atoms.

For the commercial raw material paraffins, those available at a low cost in a large amount, such as straight-run light naphtha, aromatic hydrocarbon extraction raffinate, and thermally cracked oil, are suitable. These commercial raw materials contain a relatively large amount of paraffins having not more than 5 carbon atoms, and a small amount of aromatic hydrocarbons, paraffins having 7 or more carbon atoms and naphthenes, in addition to the paraffins having 6 carbon atoms.

By isomerization, n-pentane in the raw material paraffins is converted to isopentane; n-hexane to 2,2-dimethylbutane, 2,3-dimethylbutane, 2-methylpentane and 3-methylpentane; 2-methylpentane and 3-methylpentane further to 2,2-dimethylbutane and 2,3-dimethylbutane. Cyclohexane in the raw material paraffins is also converted to methylcyclopentane.

Hydrogen fluoride and boron trifluoride as catalyst can be used in the ordinary amount in the reaction system, but practically hydrogen fluoride is used in an amount of preferably 0.5 to 10 times, particularly preferably 0.5 to 2 times the weight of total hydrocarbons present in the reaction system, and boron trifluoride is in an amount of preferably 0.01 to 1 times, particularly preferably 0.2 to 1 times the weight of total hydrocarbons present in the reaction system. The hydrogen fluoride and boron trifluoride in the catalyst layer are in the ordinary proportion by weight, but are preferably in a proportion by weight of hydrogen fluoride to boron trifluoride of 1 to 20, particularly preferably 2 to 10.

The percent isomerization of paraffin having 6 carbon atoms can be kept lower than the equilibrium percent isomerization during the reaction by conducting the reaction while continuously measuring, for example, a composition of reaction solution, or by experimentally or theoretically determining the time required for reaching the equilibrium in advance in view of relations between the composition of raw material paraffins and reaction conditions such as reaction temperature, amount of HF—$BF_3$ as the catalyst, and making the reaction time shorter than the determined time.

The present isomerization of paraffins having 6 carbon atoms in the reaction solution must be lower than the equilibrium percent isomerization, and is practically preferably 70 to 97%, particularly preferably 80 to 95% of the equilibrium percent isomerization. In the present invention, the percent isomerization and equilibrium percent isomerization of paraffins having 6 carbon atoms are values of isomerization to 2,2-dimethylbutane.

In order to obtain paraffins having a high octane number by isomerization of paraffins, thereby increasing the number of branched chains, the reaction temperature must be lower, so far as the reaction can proceed at that reaction temperature. The reaction temperature is preferably 0° to 70° C., more particularly 10° to 50° C. For example, in the isomerization of hexane, a paraffin having 6 carbon atoms to obtain a product containing the isomers and having an octane number (RON: Research Octane Number) of 80, the reaction temperature must be not more than 40° C. However, on the other hand, the reaction rate will be lower with decreasing reaction temperature, and consequently the reaction time for obtaining the predetermined percent isomerization will be prolonged.

In the isomerization of the paraffins in the presence of HF—$BF_3$ as a catalyst, the reaction rate depends upon reaction temperature, kind and amount of reaction initiator or promoter, kind and composition of raw material paraffins, and amount of HF—$BF_3$ as the catalyst. The reaction rate can be increased by increasing the reaction temperature, increasing the amount of reaction initiator or promoter, or increasing the amount of HF—$BF_3$ as the catalyst or particularly that of boron trifluoride. The increase in the amount of reaction initiator or promoter is not always advantageous in the commercial isomerization of paraffins because the reaction initiator or promoter is usually more expensive than the raw material paraffins, and side reactions are liable to take place with increasing content of the reaction initiator or promoter. In the increase in the amount of hydrogen fluoride and/or boron trifluoride as the catalyst, particularly the increase in the amount of boron trifluoride has a more remarkable action to promote the isomerization. However, the increase in the amount of boron trifluoride means an increase in the pressure of reaction system, whereas the increase in the amount of hydrogen fluoride means an increase in the liquid volume, necessitating a larger reactor. Thus, the increase in the amount of the catalyst is not always advantageous in the commercial isomerization. On the other hand, the increase in the reaction temperature is practically preferable for increasing the reaction rate, though the pressure of reaction system is slightly increased owing to the increase in vapor pressure. However, the reaction temperature must be lower so as to increase the number of branched chains and obtain a product with a high octane number, whereas the reaction temperature must be higher so as to shorten the reaction time. Therefore, it is substantially impossible to obtain a product with a high octane number for a short reaction time.

The present inventors have made further studies of shortening the reaction time, and have found that the reaction time can be shortened by carrying out the isomerization reaction at a plurality of stages and keeping the reaction temperature at a given stage lower than the reaction temperature at the preceding stage.

Another object of the present invention is to provide a process for isomerizing hydrocarbons, where unbranched, or relatively less branched paraffins having 6 carbon atoms as essential components are isomerized in the presence of HF—$BF_3$ as a catalyst, characterized by conducting the isomerization at a plurality of stages while keeping the reaction temperature at a given stage lower than the reaction temperature at the preceding stage and keeping the percent isomerization of paraffins having 6 carbon atoms at a given stage lower than the equilibrium percent isomerization of the paraffins having 6 carbon atoms at the reaction temperature at that stage.

The reaction temperature at the first stage must be such that the isomerization reaction can proceed, and is practically preferably 0° to 100° C., particularly preferably 10° to 70° C. The reaction temperature at the last stage must be such that the desired percent isomerization can be obtained, and is practically preferably 0° to 40° C., particularly preferably 10° to 30° C.

The number of stages for reaction can be appropriately selected in view of the amount of catalyst to be used, reaction temperature at each stage, reaction time, composition of raw material paraffins, use of an additive, and kind and amount of the additive when used, the degree of isomerization, etc., and is practically preferably 2 to 5, particularly preferably 2 to 3.

There is no particular restriction to the temperature difference between a given stage and the preceding stage, but it is preferable that the temperature difference should be large in the initial period of reaction, and small at the last period of reaction.

The percent isomerization of paraffins having 6 carbon atoms at each stage during the reaction must be lower than the equilibrium percent isomerization, and is practically preferably 50 to 97%, particularly preferably 80 to 95% of the equilibrium percent isomerization at the reaction temperature at each stage.

The amount of the catalyst at each stage is the same as when the isomerization is carried out at the one stage as described before.

Reaction conditions for each stage, such as the amount of the catalyst to be used, reaction temperature, reaction time, etc. can be appropriately selected in view of the composition of raw material paraffins, use of an additive, and kind and amount of the additive when used, and the degree of isomerization.

The reaction time must be shorter than the time required for making the paraffins having 6 carbon atoms have the equilibrium isomer composition at the reaction temperature at a given stage, and is practically preferably 10 to 120 minutes, particularly preferably 10 to 60 minutes per stage.

In the present invention, the isomerization reaction can be carried out continuously, semi-continuously or batchwise. Furthermore, the reaction temperature can be continuously lowered with time at the same reaction stage so that, for example, the reaction temperature can be made higher in the initial period of reaction and lower in the last period of reaction.

According to the present invention, side reactions can be prevented in the isomerization reaction of paraffins having mainly 5 to 6 carbon atoms, and paraffins with a very high octane number can be obtained for a short period of time.

Hydrogen fluoride and/or boron trifluoride can be recovered from the reaction product solution obtained according to the present invention, and reused. That is, the reaction product solution is separated into a catalyst layer and a hydrocarbon layer by settling, or centrifuge. The catalyst layer contains a relatively large amount of hydrogen fluoride and boron trifluoride, and a relatively small amount of hydrocarbons.

The catalyst layer above mentioned may be reused as such without further treatment, but it is preferable to use hydrogen fluoride and boron trifluoride after removing hydrocarbons contained in the catalyst layer.

The hydrocarbon layer contains a relatively large amount of hydrocarbons and a relatively small amount of hydrogen fluoride and boron trifluoride. Boron trifluoride is extracted from the hydrocarbon layer by bringing the hydrocarbon layer into contact with a liquid extracting agent containing at least hydrogen fluoride. The extract containing hydrogen fluoride and boron trifluoride can be reused as such or after concentration. The liquid extracting agent can contain a small amount of boron trifluoride, aromatic hydrocarbons and/or high boiling products in addition to hydrogen fluoride.

The hydrocarbon layer is separated into product hydrocarbons and a gaseous catalyst component containing boron trifluoride and hydrogen fluoride, and, in some cases, further containing a small amount of low boiling hydrocarbons by distrillation, evaporation or flashing. Boron trifluoride and hydrogen fluoride in the gaseous catalyst component are absorbed into a liquid absorbent containing at least hydrogen fluoride by contact of the gaseous catalyst component with the liquid absorbent, whereby an absorbing liquid can be obtained. The resulting absorbing liquid containing hydrogen fluoride and boron trifluoride can be reused as such or after concentration, or after making up hydrogen fluoride. The absorbent can contain boron trifluoride in addition to hydrogen fluoride.

The present invention will be described more specifically below referring to Examples.

EXAMPLE 1

47.7 g of raw material hydrocarbons shown in Table 1, 75 g of hydrogen fluoride and 46 g of boron trifluoride were mixed together and subjected to reaction in a tightly sealed reactor at 30° C. for 400 minutes, while keeping the percent isomerization of paraffins having 6 carbon atoms at 43.9% (which corresponded to 84.8% of the equilibrium percent isomerization of paraffins having 6 carbon atoms at 30° C.), whereby 46.9 g of product hydrocarbons shown in Table 1 was obtained.

Yield of the product hydrocarbons to the raw material hydrocarbons was 98.3%. The yield of the product hydrocarbons to the raw material hydrocarbons (which will be hereinafter referred to merely as "yield") is represented by the following formula:

$$\frac{\text{Weight of product hydrocarbon}}{\text{Weight of raw material hydrocarbon}} \times 100$$

TABLE 1

|  | Raw material | Product |
|---|---|---|
| | (unit: wt. %)[1] | |
| Propane and butane | 0.15 | 0.18 |
| Isopentane | 0.24 | 39.0 |
| n-Pentane | 47.1 | 7.15 |
| 2,2-dimethylbutane | 0.17 | 20.7 |
| 2,3-dimethylbutane | 0.12 | 3.12 |
| 2-methylpentane | 0.44 | 14.0 |
| 3-methylpentane | 0.51 | 5.99 |
| n-hexane | 45.1 | 3.34 |
| Methylcyclopentane | 0.40 | 1.14 |
| Cyclohexane | 5.66 | 4.87 |
| High boiling hydrocarbons having 7 or more carbon atoms | 0.11[2] | 0.480 |
| Octane number[3] | 46.0 | 88.0 |

[1] Determined by gas chromatography (this will be applicable to other examples)
[2] 2,2,4-trimethylpentane
[3] RON(this will be applicable to other examples)

EXAMPLE 2

Isomerization was carried out in the same manner as in Example 1, except that 31 g of boron trifluoride, reaction temperature of 50° C., reaction time of 90 minutes, and percent isomerization of paraffins having 6 carbon atoms of 43.1% (which corresponded to 89.3% of the equilibrium percent isomerization of the paraffins having 6 carbon atoms at 50° C.) were used, and 46.5 g of product hydrocarbons as shown in Table 2 was obtained in the yield of 97.5%.

TABLE 2

| Propane and butane | 1.21 |
|---|---|
| Isopentane | 38.5 |
| n-pentane | 7.40 |
| 2,2-dimethylbutane | 19.8 |
| 2,3-dimethylbutane | 3.07 |
| 2-methylpentane | 13.6 |
| 3-methylpentane | 5.84 |
| n-hexane | 3.64 |
| methylcyclopentane | 1.02 |
| cyclohexane | 4.07 |
| High boiling hydrocarbons having 7 or more carbon atoms | 1.04 |
| Octane number | 87.6 |

EXAMPLE 3

Isomerization was carried out at 3 stages, using 47.7 g of the same raw material hydrocarbons as used in Example 1, whereby 46.1 g of product hydrocarbons was obtained in the yield of 96.6%.

Reaction conditions and the composition of product hydrocarbons are shown in Table 3 and Table 4, respectively

TABLE 3

|  | 1st stage | 2nd stage | 3rd stage |
|---|---|---|---|
| Reaction temp. (°C.) | 60 | 40 | 25 |
| Reaction time (min.) | 30 | 40 | 60 |
| Percent isomerization of paraffins having 6 carbon atoms (%) | 38.2 | 45.4 | 49.8 |
| Percent to corresponding equilibrium percent isomerization at the reaction temperature of paraffins having 6 carbon atoms | 82.2 | 90.8 | 94.4 |
| HF in reaction solution (g) | 75 | 75 | 75 |
| BF3 in reaction solution (g) | 31 | 31 | 38 (7 g of BF3 was added after the second stage) |

TABLE 4

| Propane and butane | 1.18 |
|---|---|
| Isopentane | 35.2 |
| n-pentane | 6.91 |
| 2,2-dimethylbutane | 24.7 |
| 2,3-dimethylbutane | 5.41 |
| 2-methylpentane | 10.7 |
| 3-methylpentane | 5.72 |
| n-hexane | 3.07 |
| methylcyclopentane | 1.03 |
| cyclopentane | 4.99 |
| High boiling hydrocarbons having 7 or more carbon atoms | 1.09 |
| Octane number | 88.8 |

EXAMPLE 4

Isomerization was carried out at two stages, using 49.2 g of the same raw material hydrocarbons as used in Example 1, whereby 47.8 g of product hydrocarbons was obtained in the yield of 97.2%. Reaction conditions and the composition of product hydrocarbons are shown in Table 5 and Table 6, respectively.

TABLE 5

|  | 1st stage | 2nd stage |
|---|---|---|
| Reaction temp. (°C.) | 50 | 30 |
| Reaction time (min.) | 60 | 60 |
| Percent isomerization of paraffins having 6 carbon atoms (%) | 40.8 | 47.3 |
| Percent to the corresponding equilibrium percent isomerization at the reaction temperature of paraffins having 6 carbon atoms | 84.6 | 91.4 |
| HF in reaction solution (g) | 75 | 75 |
| BF3 in reaction solution (g) | 31 | 31 |

TABLE 6

| Propane and butane | 2.17 |
|---|---|
| Isopentane | 35.7 |
| n-pentane | 6.31 |
| 2,2-dimethylbutane | 22.9 |
| 2,3-dimethylbutane | 5.53 |
| 2-methylpentane | 10.9 |
| 3-methylpentane | 6.03 |
| n-hexane | 3.03 |
| methylcyclopentane | 1.01 |
| cyclohexane | 4.97 |
| High boiling hydrocarbons having 7 or more carbon atoms | 1.45 |
| Octane number | 89.4 |

EXAMPLE 5

50.7 g of raw material hydrocarbons shown in Table 7, 80 g of hydrogen fluoride, and 39 g of boron trifluoride were mixed together, and subjected to isomerization in a tightly closed reactor at 40° C. for 140 minutes while keeping the percent isomerization of paraffins having 6 carbon atoms at 46.0% (which corresponded to 92.0% of the equilibrium percent isomerization at 40° C. of the paraffins having 6 carbon atoms), whereby 48.9 g of product hydrocarbons shown in Table 7 was obtained in the yield of 96.4%.

TABLE 7

|  | Raw material hydrocarbons | Product hydrocarbons |
|---|---|---|
| Propane and butane | 0 | 0.21 |
| Isopentane | 0 | 0.94 |
| n-pentane | 0.30 | 0.16 |
| 2,2-dimethylbutane | 0.22 | 41.7 |
| 2,3-dimethylbutane | 0.25 | 5.71 |
| 2-methylpentane | 0.48 | 25.1 |
| 3-methylpentane | 1.16 | 12.2 |
| n-hexane | 89.9 | 5.89 |
| methylcyclopentane | 0.50 | 1.21 |
| cyclohexane | 7.09 | 5.69 |
| High boiling hydrocarbons having 7 carbon atoms | 0.10* | 1.19 |
| Octane number | 27.5 | 82.7 |

*1-hexane

EXAMPLE 6

Isomerization was carried out at three stages, using 51.1 g of the same raw material hydrocarbons as used in Example 5, whereby 50.3 g of product hydrocarbons was obtained in the yield of 96.9%. Reaction conditions and the composition of product hydrocarbons are shown in Table 8 and Table 9, respectively.

TABLE 8

|  | 1st stage | 2nd stage | 3rd stage |
|---|---|---|---|
| Reaction temp. (°C.) | 65 | 40 | 25 |
| Reaction time (min.) | 20 | 50 | 40 |
| Percent isomerization of paraffins having 6 carbon atoms (%) | 34.7 | 47.0 | 50.3 |
| Percent to corresponding equilibrium percent isomerization at the reaction temperature of paraffins having 6 carbons atoms | 75.9 | 94.0 | 95.4 |
| HF in reaction solution (g) | 80 | 80 | 80 |
| BF$_3$ in reaction solution (g) | 34 | 34 | 34 |

TABLE 9

| Propane and butane | 0.75 |
|---|---|
| Isopentane | 0.81 |
| n-pentane | 0.14 |
| 2,2-dimethylbutane | 45.3 |
| 2,3-dimethylbutane | 9.67 |
| 2-methylpentane | 19.2 |
| 3-methylpentane | 10.7 |
| n-hexane | 5.23 |
| methylcyclopentane | 1.17 |
| cyclopentane | 5.73 |
| High boiling hydrocarbons having 7 or more carbons atoms | 1.30 |
| Octane number | 83.9 |

EXAMPLE 7

Isomerization was carried out at two stages, using 47.3 g of raw material hydrocarbons shown in Table 10, whereby 46.7 g of product hydrocarbons was obtained in the yield of 97.7%. Reaction conditions are shown in Table 11.

TABLE 10

|  | Raw material hydrocarbons | Product hydrocarbons |
|---|---|---|
| Propane and butane | 0 | 0.64 |
| Isopentane | 0.54 | 79.8 |
| n-pentane | 93.6 | 12.6 |
| 2,2-dimethylbutane | 0 | 0.36 |
| 2,3-dimethylbutane | 0 | 0.11 |
| 2-methylpentane | 0 | 0.47 |
| 3-methylpentane | 0 | 0.21 |
| n-hexane | 0 | 0.08 |
| methylcyclopentane | 0.37 | 0.92 |
| cyclohexane | 5.31 | 4.49 |
| High boiling hydrocarbons having 7 or more carbon atoms | 0.18* | 0.32 |
| Octane number | 65.0 | 94.8 |

*2,2,4-trimethylpentane

TABLE 11

|  | 1st stage | 2nd stage |
|---|---|---|
| Reaction temp. (°C.) | 50 | 30 |
| Reaction time (min.) | 40 | 40 |
| Percent isomerization of paraffins having 6 carbon atoms (%) | 23.2 (78.3)* | 29.3 (86.4)* |
| Percent to corresponding equilibrium percent isomerization at the reaction temperature of paraffins having 6 carbon atoms | 48.1 (92.6)** | 56.6 (100)** |
| HF in reaction solution (g) | 78 | 78 |
| BF$_3$ in reaction solution (g) | 38 | 38 |

*:percent isomerization of paraffins having 5 carbon atoms
**:percent to corresponding equilibrium percent isomerization at the reaction temperature of paraffins having 5 carbon atoms

EXAMPLE 8

Isomerization was carried out at three stages, using 47.3 g of raw material hydrocarbons shown in Table 12, whereby 45.8 g of product hydrocarbons shown in Table 12 was obtained in the yield of 96.8%. Reaction conditions are shown in Table 13.

TABLE 12

|  | Raw material hydrocarbons | Product hydrocarbons |
|---|---|---|
| Propane and butane | 0.03 | 1.23 |
| Isopentane | 43.2 | 49.6 |
| n-Pentane | 16.8 | 7.48 |
| 2,2-dimethylbutane | 0.07 | 18.1 |
| 2,3-dimethylbutane | 0.10 | 3.96 |
| 2-methylpropane | 0.17 | 7.82 |
| 3-methylpropane | 0.43 | 3.90 |
| n-hexane | 33.2 | 1.72 |
| methylcyclopentane | 0.40 | 0.96 |
| cyclohexane | 5.42 | 4.48 |
| High boiling hydrocarbons having 7 or more carbon atoms | 0.18* | 0.75 |
| Octane number | 67.2 | 91.3 |

*2,2,4-trimethylpentane

TABLE 13

|  | 1st stage | 2nd stage | 3rd stage |
|---|---|---|---|
| Reaction temp. (°C.) | 50 | 30 | 20 |
| Reaction time (min.) | 50 | 40 | 60 |
| Percent isomerization of paraffins having 6 carbon atoms (%) | 42.1 (11.8)* | 47.9 (14.0)* | 51.0 (14.9)* |
| Percent to corresponding | 87.3 | 92.6 | 94.9 |

TABLE 13-continued

|  | 1st stage | 2nd stage | 3rd stage |
| --- | --- | --- | --- |
| equilibrium percent isomerization at the reaction temperature of paraffins having 6 carbon atoms | (93.7)** | (97.2)** | (96.8)** |
| HF in reaction solution (g) | 78 | 78 | 78 |
| BF$_3$ in reaction solution (g) | 38 | 38 | 38 |

*:percent isomerization of paraffins having 5 carbon atoms
**:percent to corresponding equilibrium percent isomerization at the reaction temperature of paraffins having 5 carbon atoms

What is claimed is:

1. A process for isomerizing hydrocarbons which comprises isomerizing a hydrocarbon mixture containing unbranched or less branched paraffins having 5 to 6 carbon atoms as main components in the presence of hydrogen fluoride and boron trifluoride as a catalyst while keeping percent isomerization of the paraffins having 6 carbon atoms lower than the equilibrium percent isomerization of the paraffins having 6 carbon atoms, on the basis of 2,2-dimethylbutane, at a given isomerization temperature.

2. A process for isomerizing hydrocarbons which comprises isomerizing a hydrocarbon mixture containing unbranched or less branched paraffins having 5 and 6 carbon atoms as main components in the presence of hydrogen fluoride and boron trifluoride as a catalyst at a plurality of stages while keeping a reaction temperature at a given stage lower than that at the preceding stage while keeping percent isomerization of the paraffins having 6 carbon atoms lower than the equilibrium percent isomerization of the paraffins having 6 carbon atoms, on the basis of 2,2-dimethylbutane, at the reaction temperature at the given stage.

3. A process according to claim 1 or 2, wherein raw material hydrocarbons further containing paraffins having not more than 5 carbon atoms, paraffins having 7 or more carbon atoms, naphthenes and/or aromatic hydrocarbons in addition to the paraffins having 6 carbon atoms are used.

4. A process according to claim 3, wherein raw material hydrocarbons containing 1 to 20% by weight of paraffins having 7 carbon atoms, 0.1 to 1% by weight of paraffins having 8 carbon atoms, not more than 0.1% by weight of paraffins having 9 or more carbon atoms, 1 to 40% by weight of naphthenes, and not more than 2% by weight of aromatic hydrocarbons in addition to the paraffins having 6 carbon atoms are used.

5. A process according to claim 1 or 2, wherein the paraffins having 6 carbon atoms is n-hexane, 2-methylpentane and/or 3-methylpentane.

6. A process according to claim 1 or 2, wherein 0.5 to 10 parts by weight of hydrogen fluoride and 0.01 to 1 part by weight of boron trifluoride are used per part by weight of total hydrocarbons present in reaction system.

7. A process according to claim 1 or 2, wherein a ratio by weight of hydrogen fluoride to boron trifluoride is 1 to 20.

8. A process according to claim 1, wherein the percent isomerization of the paraffins having 6 carbon atoms is 70 to 97% of the equilibrium percent isomerization at a given temperature of the paraffins having 6 carbon atoms.

9. A process according to claim 1, wherein the reaction temperature is 0° to 70° C.

10. A process according to claim 2, wherein the reaction temperature at first stage is 0° to 100° C.

11. A process according to claim 2, wherein the reaction temperature at last stage is 0° to 40° C.

12. A process according to claim 2, wherein number of the stages for isomerization is 2 to 5.

13. A process according to claim 2, wherein the percent isomerization of the paraffins having 6 carbon atoms at a given stage is 50 to 97% of the equilibrium percent isomerization at the reaction temperature at the stage.

14. A process according to claim 2, wherein the reaction temperature is continuously lowered with time, thereby making the reaction temperature higher in the initial period of reaction and lower in the last period of reaction.

15. A process for isomerizing a hydrocarbon mixture which comprises isomerizing a hydrocarbon mixture containing paraffins of 5 and 6 carbon atoms as main components, terminating the isomerization reaction when the percent isomerization of paraffins having 6 carbon atoms is 70 to 97% of the equilibrium percent isomerization of said paraffins of 6 carbon atoms, on the basis of 2,2-dimethylbutane, at the temperature of the isomerization reaction, and recovering the isomerization product.

* * * * *